United States Patent [19]

König

[11] 4,215,037

[45] Jul. 29, 1980

[54] PARTIALLY PROTECTED HUMAN INSULIN-A-CHAIN AND PROCESS FOR ITS MANUFACTURE

[75] Inventor: Wolfgang König, Hofheim am Taunus, Fed. Rep. of Germany

[73] Assignee: Hoechst Aktiengesellschaft, Frankfurt, Fed. Rep. of Germany

[21] Appl. No.: 940,128

[22] Filed: Sep. 6, 1978

[30] Foreign Application Priority Data

Sep. 8, 1977 [DE] Fed. Rep. of Germany ....... 2740406

[51] Int. Cl.² ........................................... C07C 103/52
[52] U.S. Cl. ............................ 260/112.5 R; 260/112.7
[58] Field of Search ....................... 260/112.7, 112.5 R

[56] References Cited

U.S. PATENT DOCUMENTS 3,883,500  5/1975  Geiger et al. ..................... 260/112.7
3,994,871  11/1976 Kamber et al. ............... 260/112.5 R

FOREIGN PATENT DOCUMENTS 1301514  4/1970  United Kingdom ............. 260/112.5 R

OTHER PUBLICATIONS

Cohen, Synthetic Studies on the A and B of Insulin, 9, (2), 1964, pp. 238–241.

*Primary Examiner*—Delbert R. Phillips
*Attorney, Agent, or Firm*—Curtis, Morris & Safford

[57] ABSTRACT

Partially protected human insulin-A-chain suitable as intermediate for insulin synthesis and process for its manufacture by reacting the partially protected peptide fragment 6 to 26 of the insulin-A-chain with the peptide fragment 1 to 5 containing an N-terminal amino protective group capable of being split off by 5% strength trifluoroacetic acid in methylene chloride.

3 Claims, No Drawings

PARTIALLY PROTECTED HUMAN INSULIN-A-CHAIN AND PROCESS FOR ITS MANUFACTURE

The synthesis of insulins, using as starting material the two peptide chains A and B, can be carried out in an especially advantageous manner with the aid of bridge reagents which link the α-amino group in A1 with the ε-amino group in B29 (cf. Biochem. Biophys. Comm. 55, pages 60 to 66 (1973)). The subsequent oxidation of the mercapto groups to disulfides and the splitting off of the bridge reagent results in a much better yield of insulin than the oxidation of isolated chains. In order that the chains can be linked at the desired positions they have to be used in a suitably protected form.

According to J.Am.Chem.Soc. 89, page 4505 (1967) the sequence of the human insulin-A-chain was synthetized, but for the coupling with bridge reagents this peptide is less suitable.

It is the object of the present invention to provide a partially protected human insulin-A-chain of the formula I H-Gly-Ile-Val-Glu(OBu$^t$)-Gln-Cys(Trt)-Cys(Trt)-Thr(Bu$^t$)-Ser(Bu$^t$)-Ile-Cys(Trt)-Ser-Leu-Tyr(-Bu$^t$)Gln-Leu-Glu(OBu$^t$)-Asn-Tyr(Bu$^t$)-Cys(Trt)-Asn-OBu$^t$.

It is another object of the present invention to provide a process for the manufacture of the peptide of formula I which comprises condensing the peptide of the formula II H-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ by the dicyclohexylcarbodiimide method with the addition of N-hydroxy compounds with the peptide of the formula III X-Gly-Ile-Val-Glu(OBu$^t$)-Gln-OH in which X is an amino protective group capable of being split off by 5% trifluoroacetic acid in 95% of methylene chloride and selectively splitting off the N-terminal protective group X from the peptide obtained with about 5% strength trifluoroacetic acid in methylene chloride.

A suitable N-hydroxy compound to be added in the condensation with dicyclohexylcarbodiimide (DCC) is especially 1-hydroxybenzotriazole (HOBT). Instead of HOBT there may also be used N-hydroxysuccinimide, 3-hydroxy-4-oxo-3,4-dihydro-1,2,3-benzotriazine or 2-hydroxyimino-2-cyano-acetic acid ethyl ester. The coupling reactions are carried out at 0° C. to room temperature in a polar solvent, for example dimethylformamide or dimethylacetamide or a mixture thereof. N-terminal protective groups X that can be used are the 3,5-dimethoxy-α,α-dimethylbenzyloxycarbonyl group (Ddz), the diphenyl-isopropyloxycarbonyl group (Bpoc) and the trityl group.

The protective group X is selectively split off in about 5% strength trifluoroacetic acid-methylene chloride solution, to which a small amount of water (about 1%) and anisole (about 10%) or compounds having a similar action can be added.

The peptide of formula II can be prepared and further reacted according to the invention to give the peptide of formula I by the following reaction scheme I. In all preliminary stages the Ddz group is preferably used as protective group at the amino end and after removal thereof the condensation with the next Ddz peptide takes place.

For the synthesis of the precursors the Ddz group known from "Annalen der Chemie" 763, pages 162 to 172 (1972) is especially suitable since, on the one hand, it can be readily split off in weakly acid solution and, on the other, it is stable to catalytic hydrogenation, which is surprising. Thus, for example, benzyl or nitrobenzyl (Nb) esters, can be split selectively by catalytic hydrogenation in the presence of the Ddz group.

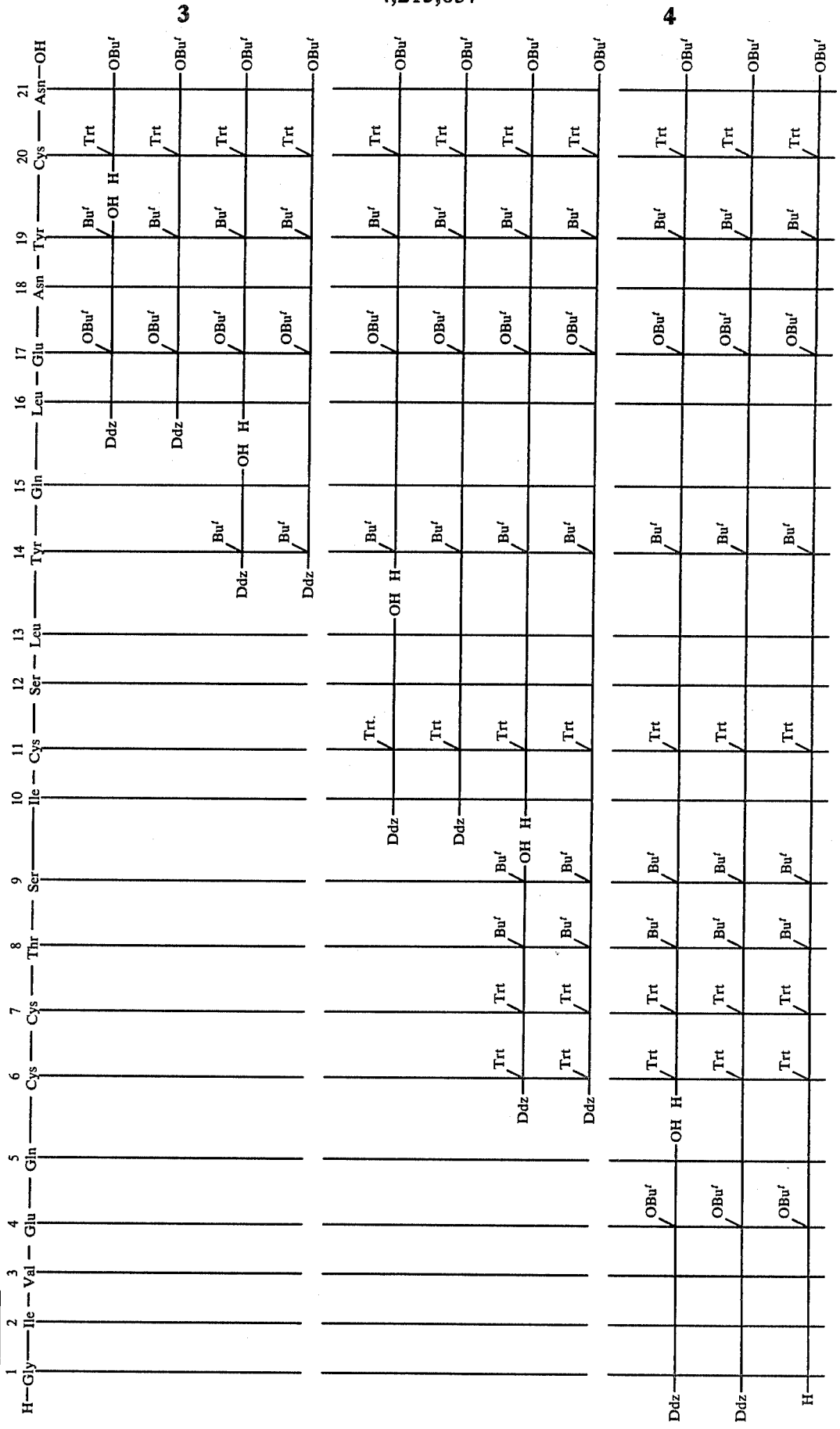

The individual peptide fragments to be used according to scheme I were prepared as follows: H-Cys(Trt)-Asn-OBu$^t$ (fragment 20–21) was prepared as described in Helv.Chim.Acta 54, pages 398 to 422 (1971). Ddz-Leu-Glu(OBu$^t$)-Asn-Tyr(Bu$^t$)-OH (fragment 16–19) was prepared according to reaction scheme II by stepwise synthesis with Z(Z=Benxyloxycarbonyl)- and Ddz-amino acid-2,4,5-trichlorophenyl (Tcp) ester with HOBt catalysis. The intermediate Z-protective groups were removed by catalytic hydrogenation.

Reaction Scheme II

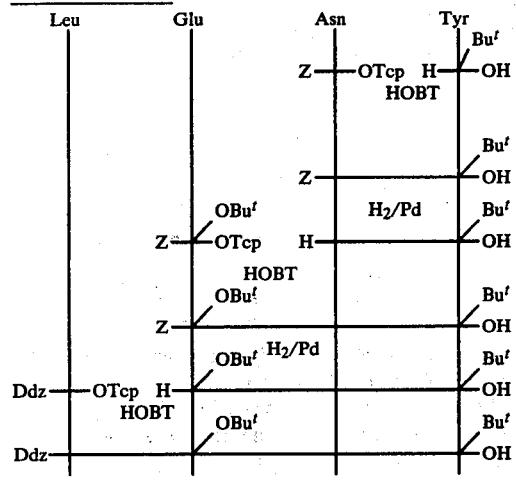

Ddz-Try(Bu$^t$)-Gln-OH (fragment 14–15) was prepared by catalytic hydrogenation of Ddz-Tyr(Bu$^t$)-Gln-ONb Ddz-Ile-Cys(Trt)-Ser-Leu-OH (fragment 10–13) was prepared by reaction of Ddz-Ile-OTcp with the known H-Cys(Trt)-Ser-Leu-OH (Chem. Ber. 103, pages 2034 to 2040 (1970)). Ddz-Cys(Trt)-Cys(Trt)-Thr(Bu$^t$)-Ser-(Bu$^t$)-OH (fragment 6–9) was synthesized analogous to Reaction Scheme III Reaction scheme III

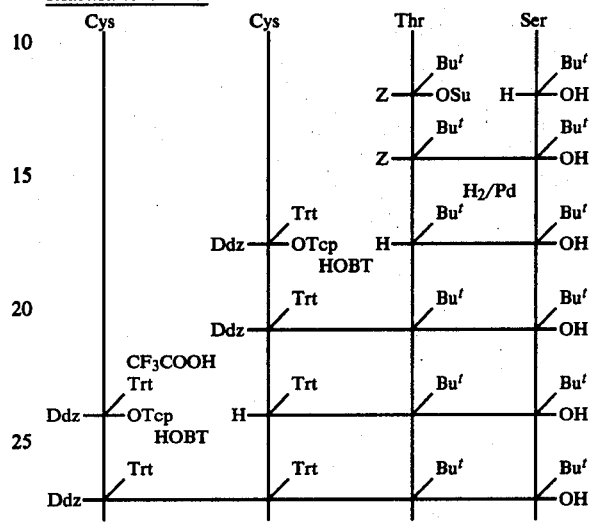

The other component to be used according to the invention, i.e. fragment 1 to 5 of formula III Ddz-Gly-Ile-Val-Glu-(OBu$^t$)-Gln-OH can be prepared according to two different methods, namely scheme IV or V.

Reaction scheme IV

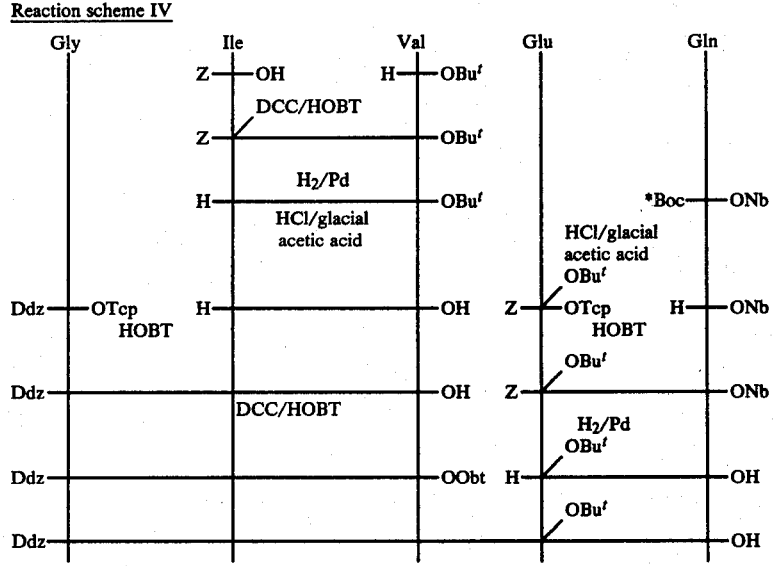

*Boc = tert.-Butyloxycarbonyl

Reaction scheme V

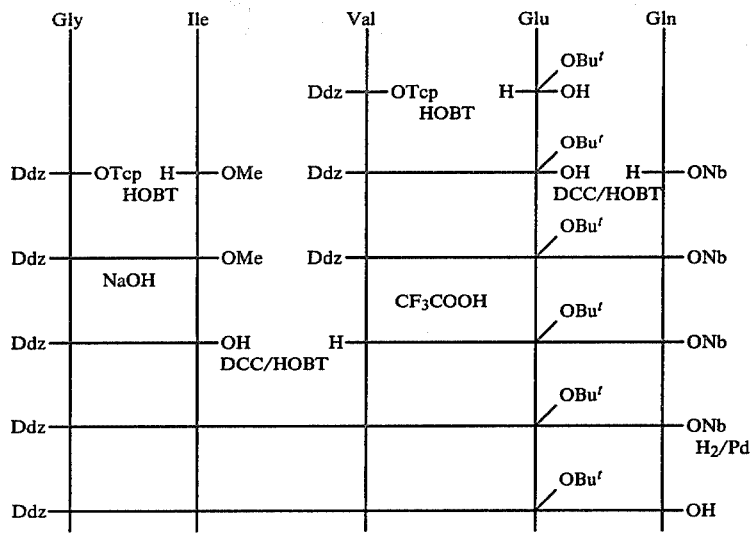

The following Example illustrates the invention.

(I) Synthesis of fragment 16–19

Ddz-Leu-Glu(OBu$^t$)-Asn-Tyr(Bu$^t$)-OH

1. Ddz-Leu-OTcp 33.3 g (94.3 mmols) of Ddz-Leu-OH (Ann. Chem. 1973, pages 1652 to 1662) and 19.6 g (0.1 mol) of 2,4,5-trichlorophenol were dissolved in 350 ml of ethyl acetate. At 0° C. a solution of 20.4 g of DCC in 60 ml ethyl acetate was added and the mixture was stirred for 3 hours at 0° C. and overnight at room temperature. The precipitated dicyclohexyl urea was filtered off with suction and the filtrate was concentrated. The residue crystallized with petroleum ether when kept overnight in a cooling chamber.

Yield: 39.2 g (73.6% calculated on H-Leu-OMe.HCl). m.p. 108° C., $[\alpha]_D^{29} = -31.3°$ (c=1, in dimethylacetamide)

$C_{24}H_{28}NO_6Cl_3$ (532.83)

Calc. C 54.10; H 5.30; N 2.62; Cl 20.01; Found C 54.7; H 5.4; N 2.9; Cl 19.3.

2. Ddz-Leu-Glu(OBu$^t$)-Asn-Tyr(Bu$^t$)-OH.0.5 H$_2$O 27.7 g (50 mmols) H-Glu(OBu$^t$)-Asn-Tyr(Bu$^t$)-OH (Chem. Ber. 110, pages 1 to 11 (1977)) were suspended in 150 ml dimethylformamide. After addition of 6.75 g (50 mmols) of HOBt, dissolution took place. The solution was cooled to 0° C. and 6.5 ml (50 mmols) of N-ethylmorpholine and 28 g (52.5 mmols) of Ddz-Leu-OTcp were added. Next, the mixture was stirred for 1 hour at 0° C. and for 3 hours at room temperature. A fluoram test indicated that the amino component had not yet fully reacted. A further 1.3 g (2.5 mmols) of Ddz-Leu-OTcp were added and the mixture was left to react for some hours at room temperature. When the mixture was fluoram-negative, it was worked up.

The solvent was removed in a high vacuum and the residue dissolved in ethyl acetate. The solution was adjusted to pH 4 with icecold citrate buffer (pH 3) and then the ethyl acetate phase was washed once with citrate buffer (pH 4) and twice with water. The reaction mixture was dried over Na$_2$SO$_4$ and concentrated. The residue was triturated with a mixture of ether and petroleum ether (1:1), placed in the cooling chamber for a few hours and filtered with suction.

Yield 35.35 g (80.25%), m.p. 222°–223° C.

$[\alpha]_D^{25} = -23.7°$ (c=1, in methanol)

$C_{44}H_{65}N_5O_{13}.0.5$ H$_2$O (881.04)

Calc. C 60.00; H 7.55; N 7.95; Found C 60.0; H 7.6; N 8.0.

(II) Synthesis of fragment 14–15:

Ddz-Try(Bu$^t$)-Gln-OH

1. H-Tyr(Bu$^t$)-OMe.HCl 300 g (778 mmols) of Z-Tyr(Bu$^t$)-OMe (Ann. Chem. 696, page 226 (1966)) were dissolved in 1 l of methanol and catalytically hydrogenated (Pd/BaSO$_4$ catalyst) at pH 4.5 on the autoburette (addition of about 2 N methanolic HCl). When the hydrogenation was complete, the catalyst was filtered off with suction and the filtrate was concentrated. The residue was triturated with ether.

Yield 189.2 g (84.5%).

m.p. 154°–156° C., $[\alpha]_D^{22} = +15.0°$ (c=1, in methanol)

$C_{14}H_{22}NO_3Cl$ (287.79)

Calc. C 58.43; H 7.7; N 4.86; Found C 58,6; H 7,6; N 4,8.

2. Ddz-Tyr(Bu$^t$)-OMe

While cooling with ice and stirring, 35 ml (0.25 mol) of triethylamine and 79.5 g (0.3 mol) of Ddz-azide were added to a solution of 71.95 g (0.25 mol) of H-Tyr(Bu$^t$)-OMe.HCl in 110 ml of dimethylformamide. After 5 minutes, a further 35 ml (0.25 mol) of triethylamine were added, the ice bath was removed and the mixture allowed to warm up to room temperature. After 30 minutes, 7 ml (50 mmols) of triethylamine were added and stirring was continued for 3 hours at room temperature. The mixture was left to stand at room temperature overnight and the partitioned between 250 ml of ethyl acetate and 250 ml of water. After the addition of ice, the ethyl acetate phase was washed three times, each time with 125 ml of icecold citrate buffer (pH 3), once with 250 ml of saturated sodium bicarbonate solution and once with 125 ml of water, dried over Na$_2$SO$_4$ and concentrated. The residue was dried in a high vacuum. Yield 118.2 g of oil (99.8%).

(3) Ddz-Tyr(Bu$^t$)-OH

The oily Ddz-Tyr(Bu$^t$)-OMe (118.2 or 249.5 mmols) obtained as described sub 2) were dissolved in 500 ml of 1,2-dimethoxyethane and a small amount of thymolphthalein was added. While stirring, 250 ml of 1 N sodium hydroxide solution were added dropwise and the mixture was stirred until the blue color thereof had faded. 120 ml of 1 N NaOH were then added gradually in portions until the blue color had disappeared (the additional consumption of sodium hydroxide solution was a result of the acetate content of the starting product). Next, the solution was neutralized with citric acid and concentrated.

Ice water was added to the residue and in the mixture a pH of 3.5 was adjusted by adding citric acid at 0° C. The oil formed was taken up in ethyl acetate and the ethyl acetate phase was shaken, twice with 200 ml of citrate buffer (pH 4) and twice with 200 ml of water. The ethyl acetate phase was then dried over $Na_2SO_4$, distilled off and dried in a high vacuum. A yellow-white amorphous substance was obtained. Yield 99.5 g (86.8%).

m.p. ca. 38°–40° C., $[\alpha]_D^{22} = +41.5°$ (c=1, in methylene chloride)

$C_{25}H_{33}NO_7$ (459.55)

Calc. C 65.34; H 7.24; N 3.05; Found C 65.0; H 7.3; N 3.0.

4. Ddz-Tyr(Bu$^t$)-Gln-ONb 6.4 ml (50 mmols) of N-ethylmorpholine and 10.5 g of DCC were added at −3° C. to a solution of 25.24 g (55 mmols) of Ddz-Tyr(But)-OH, 15.88 g (50 mmols) of H-Gln-ONb.HCl (Chem. Ber. 110, pages 1 to 11 (1977)) and 6.75 g of HOBT monohydrate in 100 ml of dimethylformamide, the mixture was stirred for 1 hour at 0° C. and for 6 hours at room temperature and left to stand overnight at room temperature. The precipitate was filtered off with suction and the filtrate was concentrated. The resulting oil was dissolved in ethyl acetate and the solution washed successively with $NaHCO_3$ solution, citrate buffer (pH 3) and water, dried over $Na_2SO_4$) and concentrated. The oil was triturated with petroleum ether until it had powder form and filtered off with suciton. For further purification, the substance was boiled three times, each time with 100 ml of diisopropyl ether and decanted. Finally, it was triturated with cold diisopropyl ether, filtered off with suction and washed with petroleum ether.

Yield 32.8 g (91%), m.p. 80°–90° C.

$[\alpha]_D^{22} = +15.1°$ (c=1, in methanol)

$C_{37}H_{46}N_4O_{11}$ (722.81)

calc. C 61.48; H 6.41; N 7.75; found C 61.3; H 6.7; N 7.9.

(5) Ddz-Try(Bu$^t$)-Gln-OH-DCHA 5 ml of water and Pd/BaSO$_4$ catalyst were added to a solution of 32.5 g (45 mmols) of Ddz-Tyr(Bu$^t$)-Gln-ONb in 500 ml of methanol and the mixture was hydrogenated for 7 hours. The catalyst was then removed by suction filtration and the filtrte was concentrated. The remaining oil was dissolved in 250 ml of ethyl acetate and 11.3 ml (55 mmols) of dicyclohexylamine (DCHA) were added. The whole was kept for a few hours in a cooling chamber and then the precipitate was filtered off with suction. The filter residue was triturated with ethyl acetate in a mortar, filtered off with suction and dried in vacuo.

Yield 27 g (78%)

m.p. 170°–171° C., $[\alpha]_D^{23} = +10.20°$ (c=1, in methanol)

$C_{42}H_{64}N_4O_9$ (769.0)

calc. C 65.6; H 8.39; N 7.28; found C 65.4; H 8.5; N 7.3.

(6) Ddz-Tyr(Bu$^t$)-Gln-OH 2.9 g (3.77 mmols) of Ddz-Tyr(Bu$^t$)-Gln-OH-DCHA were partitioned between ethyl acetate and citrate buffer (pH 3). The ethyl acetate phase was washed neutral with water, dried over $Na_2SO_4$ and concentrated. An amorphous product was obtained.

Yield 2 g (90%)

m.p. 110°–115° C., $[\alpha]_D^{22} = +19.8°$ (c=1, in methanol)

$C_{30}H_{41}N_3O_9$ (587.68)

calc. C 61.31; H 7.03; N 7.15; found C 60.6; H 7.2; N 7.0.

III. Synthesis of fragment 10–13

Ddz-Ile-Cys(Trt)-Ser-Leu-OH

1. Ddz-Ile-OTcp

A cold solution of 52 g (252 mmols) of DCC in 175 ml of ethyl acetate was added to a solution, cooled to 0° C., of 87 g (246 mmols) of Ddz-Ile-OH (Ann. Chem. 763, pages 162 to 172 (1972)) and 48.6 g (246 mmols) of 2,4,5-trichlorophenol in 700 ml of ethyl acetate. The mixture was stirred for 3 hours at 0° C. and left to stand overnight at room temperature. The dicyclohexyl urea was filtered off and the filtrate concentrated in vacuo. The residue crystallized in petroleum ether.

Yield 105.6 g (80.5%), m.p. 92°–94° C.

$[\alpha]_D^{22} = -22.6°$ (c=1, in methanol)

$C_{24}H_{28}NO_6Cl_3$ (532.86)

calc. C 54.10; H 5.30; N 2.63; Cl 19.96; found C 54.4; H 5.4; N 2.8; Cl 19.5.

(2) Ddz-Ile-Cys(Trt)-Ser-Leu-OH.1 H$_2$O 63.95 g (120 mmols) of Ddz-Ile-OTcp were added at room temperature to a solution of 69.8 g (120 mmols) of H-Cys(Trt)-Ser-Leu-OH monohydrate (Chem. Ber. 103, pages 2034 to 2040 (1970)) and 16.2 g (120 mmols) of HOBT in 300 ml of dimethylformamide and the mixture was stirred for 4 hours at room temperature. If tripeptide was still present a further 5.33 g (10 mmols) of Ddz-Ile-OTcp were added. The mixture was kept overnight at room temperature and the solvent was distilled off in vacuo. The remaining oil was partitioned between 400 ml of ethyl acetate and 250 ml of saturated sodium bicarbonate solution. The sodium salt of the Ddz-tetrapeptide remained in the ethyl acetate phase, which was cooled and shaken successively with about 120 ml of 1 N citric acid solution (after shaking, the aqueous phase should have a pH of about 3 to 4), 150 ml of citrate buffer (pH 3) and twice with 200 ml of water. The ethyl acetate phase was then dried over $Na_2SO_4$ and concentrated in vacuo.

The residue was triturated with petroleum ether and filtered off with suction.

Yield 99.8 g (90%), m.p. (130) 135°–140° C. (decomposition)

$[\alpha]_D^{22} = 34.1°$ (c=1, in methanol)

$C_{49}H_{62}N_4O_{10}S.1$ H$_2$O (917.1)

calc. C 62.93; H 7.11; N 6.02; S 3.42; found C 63.0; H 6.8; N 5.8; S 3.4.

(IV) Synthesis of fragment 6 to 9

Ddz-Cys(Trt)-Cys(Trt)-Thr(Bu$^t$)-Ser(Bu$^t$)-OH

1. Z-Thr(Bu$^t$)-Ser(Bu$^t$)-OH 12.8 ml (0.1 mol) of N-ethylmorpholine and 40.6 g (0.1 mol) of Z-Thr(Bu$^t$)-OSu (Hoppe Seyler's Z.Physiol. Chem. 346, page 60, (1966)) were added at 0° C. to a suspension of 16.1 g (0.1 mol) of H-Ser(But)-OH (Chem. Ber. 97, page 2490 (1964)) in 100 ml of dimethylformamide, the mixture was stirred for 5 hours at room temperature and left to stand at room temperature overnight. When no H-Ser(Bu$^t$)-OH could be detected by thin layer chromatography, undissolved matter, if any, was filtered off, the filtrate was concentrated and the residue was partitioned between ether and 110 ml of 1 N citric acid. The ethereal phase was washed once again with 100 ml of 0.5 N citric acid and then washed neutral with water or NaCl solution. The ethereal phase was dried over Na$_2$SO$_4$, concentrated and dried in a high vacuum. Yield 32.5 g of an amorphous product (72%).

$[\alpha]_D^{22} = +24.1°$ (c=1, in methanol)
C$_{22}$H$_{36}$N$_2$O$_7$ (452.55)
calc. C 61.04; H 8.02; N 6.19;
found C 60.3; H 7.4; N 6.2.

2. H-Thr(Bu$^t$)-Ser(Bu$^t$)-OH.HCl 25 g (55.24 mmols) of Z-Thr(Bu$^t$)-Ser(Bu$^t$)OH were dissolved in 200 ml of methanol and catalytically hydrogenated (pH 4.5) on an autotitrator with the addition of methanolic HCl. When hydrogenation was complete, the Pd/BaSO$_4$ catalyst was removed by suction filtration, the filtrate was concentrated and dried in a high vacuum. Yield 21.1 g of an amorphous product (19.60 g ≙100%).

$[\alpha]_D^{27} = +27°$ (c=1, in methanol)
C$_{15}$H$_{31}$N$_2$C$_5$Cl (354.9)
calc. C 50.77; H 8.80; N 7.89; found C 50.9; H 8.8; N 7.8.

3. Ddz-Cys-(Trt)-OH 28 ml (0.2 mol) of triethylamine and 26.5 g (0.1 mol) of Ddz-azide were added to a suspension of 36.4 g (0.1 mol) of H-Cys(Trt)-OH (J.Org.Chem. 30, page 1340 (1965)) in 200 ml of dimethylformamide. The mixture was stirred for 24 hours at 40° C., the solution was then concentrated and the residue partitioned between 100 ml icecold 1 N citric acid and ethyl acetate. The ethyl acetate phase was shaken with citrate buffer (pH 3) and NaCl solution, dried over Na$_2$SO$_4$, concentrated and dried in a high vacuum. Yield 37.6 g of an amorphous product (64%).

$[\alpha]_D^{22} = +27.0°$ (c=1, in methanol)
C$_{34}$H$_{35}$NO$_6$S (585.7)
calc. C 69.72; H 6.02; N 2.39; found C 69.3; H 6.3; N 2.6.

4. Ddz-Cys(Trt)-OTcp 2.3 g of DCC dissolved in 15 ml of tetrahydrofuran were added at 0° C. to a solution of 5.9 g (about 10 mmols) Ddz-Cyst(Trt)-OH and 2.2 g (11 mmols) of 2,4,5-trichlorophenol in 50 ml of absolute tetrahydrofuran, the whole was stirred for 2 hours at 0° C. and left to stand overnight at room temperature. The DC urea (DC=dicyclohexyl) was filtered off with suction and the solution was concentrated. The residue was dissolved in methylene chloride and filtered over 100 g of silica gel 60. The filtrate was eluted with methylene chloride. Yield 6.2 g of an amorphous product (81%).

$[\alpha]_D^{22} = +10.3°$ C. (c=1, in methanol).
C$_{40}$H$_{36}$Cl$_3$NO$_6$S (765.17)
calc. C 62.79; H 4.74; N 1.83; S 4.19; found C 61.0; H 4.7; N 1.7; S 4.2.

According to the above carbon, hydrogen, and nitrogen analysis the substance was found to have a purity of 97%.

5. Ddz-Cys(Trt)-Thr(Bu$^t$)-Ser(Bu$^t$)-OH 12.8 ml (0.1 mol) of N-ethylmorpholine and 76.5 g (0.1 mol) of Ddz-Cys(Trt)-OTcp were added at 0° C. to a solution of 31.8 g (0.1 mol) of H-Thr(But)-OH (or more according to the water or acid content) and 13.5 g of HOBT (0.1 mol) in 100 ml of dimethylformamide. The mixture was then stirred for about 6 hours at room temperature and the solution concentrated in high vacuum. The residue was partitioned between ice water and ethyl acetate and the ethyl acetate phase was shaken with NaHCO$_3$ solution. The sodium salt of Ddz-Cys(Trt)-Thr(Bu$^t$)-Ser-(Bu$^t$)-OH remained in the ethyl acetate phase, which was then shaken at 0° C. with 100 ml of 1 N citric acid and 100 ml of citrate buffer (pH 3) and washed neutral with water. The ethyl acetate phase was dried over Na$_2$SO$_4$, concentrated and the residue was dried in a high vacuum. For further purification the substance was recrystallized from ether/petroleum ether by slowly adding dropwise the ethereal solution to the petroleum ether.

Yield 44.5 g (50%), 116°–128° C. (decomposition)
$[\alpha]_D^{22} = +25.5°$ (c=1, in methanol)
C$_{49}$H$_{63}$N$_3$O$_{10}$S (886.13)
calc. C 66.42; H 7.17; N 4.74; found C 66.1; H 7.4; N 4.7.

6. H-Cys-(Trt)-Thr(Bu$^t$)-Ser(Bu$^t$)-OH-triluoroacetate 8.8 ml (10 mmols) of Ddz-Cys(Trt)-Thr(Bu$^t$)-Ser(-Bu$^t$)-OH were dissolved at room temperature in a mixture of 8.75 ml (0.1 mol) of trifluoroacetic acid, 1.75 ml of water and 165 ml of methylene chloride (about 175 ml of 5% strength trifluoroacetic acid in methylene chloride with 1% of water). The mixture was left to stand for 1.5 hours at room temperature and then neutralized with 8.85 ml (0.11 mol) of pyridine. The solution was concentrated and the residue partitioned between ethyl acetate and water. The ethyl acetate phase was washed twice with water, dried over Na$_2$SO$_4$ and concentrated. The residue was dissolved in a small amount of ether and the solution was slowly dropped into petroleum ether. Yield 4.2 g (54%).

m.p. 85°–95° C. (decomposition)
$[\alpha]_D^{22} = +68.5°$ (c32 1, in methanol)
C$_{37}$H$_{49}$N$_3$O$_6$S.CF$_3$COOH (777.9)
calc. C 60.21; H 6.48; N 5.40; S 4.12; found C 60.7; H 6.7; N 5.2; S 4.2.

7. Ddz-Cys(Trt)-(Cys(Trt)-Thr(Bu$^t$)-Ser(Bu$^t$)-OH 0.9 ml (0.7 mmol) of N-ethylmorpholine and 5.35 g (7 mmols) of Ddz-Cys(Trt)-OTcp were added at 0° C. to a solution of 5.3 g (6.8 mmols) of H-Cys(Trt)-THr(Bu$^t$)-Ser-(Bu$^t$)-OH-trifluoroacetate and 0.95 g (0.7 mmol) of HOBT in 15 ml of dimethylformamide. The mixture was stirred for 14 hours at room temperature and the solution was concentrated as soon as the tripeptide had reacted. (If unreacted tripeptide can still be detected a small amount of Ddz-Cys-(Trt)-OTcp must be added.) The residue was taken up in ethyl acetate, the ethyl acetate phase was washed successively with 10 to 20 ml of saturated NaHCO$_3$ solution, 7 ml 1 N citric acid and 10 ml of citrate buffer (pH 3), washed neutral with NaCl solution, dried over Na$_2$SO$_4$ and concentrated. The residue was triturated with petroleum ether. For further purification the reaction product was precipitated from ether/petroleum ether or stirred with diisopropyl ether. It it also possible to reprecipitate from methanol/water.

Yield 6 g (71%)

m.p. 118°–130° C. (decomposition), $[\alpha]_D^{22} = +11.6°$ (c=1, in methanol)

C$_{71}$H$_{82}$N$_4$O$_{11}$S$_2$ (1231.6)

calc. C 69.25; H 6.71; N 4.55; S 5.21; found C 67.2; H 6.3; N 4.1; S 5.3.

According to CHN analysis the substance had a purity of about 97% only.

V. Synthesis of fragment 1–5

Ddz-Gly-Ile-Val-Glu(OBu$^t$)-Gln-OH

1. Ddz-Val-OTcp

A solution of 72.1 g (0.35 mmol) of DCC in 100 ml of ethyl acetate were added at 0° C. to a solution of 113.3 g (0.334 mmol) of Ddz-Val-OH (Liebigs Ann. 763, pages 162 to 172 (1972)) and 65.9 g (0.334 mmol) 2,4,5-trichlorophenol in 300 ml of ethyl acetate. The mixture was stirred for 1 hour at 0° C. and for 3 hours at room temperature. The DC urea was filtered off with suction and the filtrate was concentrated. The residue was crystallized with petroleum ether. Yield 111.45 g (64%), m.p. 73°–76° C.

$[\alpha]_D^{25} = -28.7°$ (c=1, in methanol).

C$_{23}$H$_{26}$NO$_6$Cl$_3$ (518.84)

calc. C 53.24; H 5.05; N 2.70. found C 53.5; H 5.2; N 2.9.

2. Ddz-Val-Glu(OBu$^t$)-OH 19.2 ml (150 mmols) of N-ethylmorpholine and 77.8 g of Ddz-Val-OTcp were added to a solution of 30.5 g (150 mmols) of H-Glu(OBu$^t$)-OH and 20.25 g (130 mmols) of HOBT in 200 ml of dimethylformamide. The mixture was stirred for 4 hours at room temperature. When no more HGlu(Bu$^t$)-OH could be detected in the thin layer chromatogram, the reaction mixture was concentrated in a high vacuum (otherwise the reaction must be completed by adding a small amount of Ddz-Val-OTcp). The resulting oil was partitioned between 300 ml of ethyl acetate and 300 ml of water. The ethyl acetate phase was shaken twice with 150 ml each of citrate buffer (pH 3) and once with 150 ml of water, dried over Na$_2$SO$_4$ and concentrated. Yield 138.7 g (78.7 g ≙ 100%). The resulting oil was further reacted as 150 mmols without further purification and characterization.

C$_{26}$H$_{40}$N$_2$O$_9$ (524.6)

3. Ddz-Val-Glu(OBu$^t$)-Gln-ONb 19.2 ml (150 mmols) of N-ethylmorpholine and 33 g (160 mmols) of DCC were added at 0° C. to the solution of crude, contaminated Ddz-Val-Glu(OBu$^t$)-OH, (138.7 g ≙ 150 mmols), 47.65 g (150 mmols) of H-Gln-ONb.HCl and 20.25 g (150 mmols) HOBt in 450 ml dimethylformamide. The mixture was stirred for 1 hour at 0° C. and for 4 hours at room temperature. It was then left to stand overnight at room temperature, the precipitate was filtered off with suction and the filtrate was concentrated in a high vacuum. The resulting oil was partitioned between 300 ml of ethyl acetate and 300 ml of water. The ethyl acetate phase was successively shaken with saturated NaHCO$_3$ solution, citrate buffer (pH 3), saturated NaHCO$_3$ solution and water, dried over Na$_2$SO$_4$ and concentrated. The oil crystallized with ether and was washed with ether. Yield 110.95 g (94%), m.p. 135°–138° C., 138°–142° C.

$[\alpha]_D^{22} = -49.4°$ (c=1, in methanol)

C$_{38}$H$_{53}$N$_5$O$_{13}$ (787.9)

calc. C 57.93; H 6.78; N 8.89; found C 57.8; H 7.0; N 9.2.

4. H-Val-Glu(OBu$^t$)-Gln-ONb-trifluoroacetate 39.4 g (50 mmols) of Ddz-Val-Glu(OBu$^t$)-Gln-ONb were dissolved in a mixture of 875 ml of a 5% strength trifluoroacetic acid/methylene chloride solution (with 1% of water) (500 mmols trifluoroacetic acid) and 87.5 ml of anisole. The mixture was left to stand for 30 minutes at room temperature, neutralized with 50 ml of pyridine, concentrated and dried in a high vacuum. The residue was partitioned between ethyl acetate and water. The ethyl acetate phase was shaken twice with a small amount of water, dried over Na$_2$SO$_4$ and concentrated. The residue was triturated with ether and dried in a high vacuum. Yield 23.6 g of amorphous substance (69%).

$[\alpha]_D^{24} = -5.3°$ (c=1, in methanol)

C$_{26}$H$_{39}$N$_5$O$_9$·CF$_3$COOH (679.69)

calc. C 49.48; H 5.93; N 10.30; found C 50.0; H 5.8; N 10.1.

5. Ddz-Gly-OTcp

A solution of 16.5 g (80 mmols) of DCC in 50 ml of ethyl acetate was added at 0° C. to a solution of 23.8 g (about 80 mmols) of Ddz-Gly-OH (Liebigs Ann. 763, pages 162 to 172 (1972)) and 16 g (about 80 mmols) of 2,4,5-trichlorophenol in 150 ml of ethyl acetate. The mixture was left to stand overnight at room temperature, the precipitate was filtered off with suction and the filtrate was concentrated. The residue was crystallized with petroleum ether. The mixture was left to stand for 6 hours in the cooling chamber. The residue was filtered off with suction and washed with petroleum ether. Yield 36.3 g (95%).

m.p. (111°–115° C.

C$_{20}$H$_{20}$NO$_6$Cl$_3$ (476.76)

calc. C 50.39; H 4.23; N 2.94; found C 50.8; H 4.3; N 2.95.

6. Ddz-Gly-Ile-OMe

To a solution of 14.54 g (80 mmols) of H-Ile-OMe.HCl and 10.8 g (80 mmols) of HOBT in 50 ml of dimethylformamide there were added 10.3 ml (80 mmols) of N-ethylmorpholine at −3° C. and 40 g (84 mmols) of Ddz-Gly-OTcp at 0° C. The mixture was stirred for 3 hours at room temperature and then left to stand overnight. On the following day a small amount of H-Ile-OMe was still detectable in the thin layer chromatogram. Therefore, another 2.86 g (6 mmols) of Ddz-Gly-OTcp were added and the mixture was stirred. After 5 hours no more H-Ile-OMe could be detected. The solution free from H-Ile-OMe (DC) was concentrated in a high vacuum and the resulting oil was partitioned between ethyl acetate and water. The ethyl acetate solution was successively washed with saturated NaHCO$_3$ solution, citrate buffer (pH 3), NaHCO$_3$ solution and water and dried over Na₂SO₄. The ethyl acetate solution was filtered over 400 g of basic Al₂O₃, the eluate was concentrated and dried in a high vacuum. Yield 30.6 g of viscous oil (90%).

$[\alpha]_D^{25} = -6.8°$ (c=1, in methanol)

$C_{21}H_{32}N_2O_7$ (424.5)

calc. C 59.42; H 7.60; N 6.60; found C 59.1; H 7.7; N 6.3.

7. Ddz-Gly-Ile-OH 10 g (23.56 mmols) of Ddz-Gly-Ile-OMe were dissolved in a mixture of 24 ml of dioxane and 8 ml of water and titrated with 1 N NaOH against thymolphthalein as indicator. Over 23 ml were consumed depending on the acetic acid content. After neutralization with citric acid, the dioxane was distilled off. The residue was taken up in water and a pH of 3 was adjusted at 0° C. with 2 N citric acid. If necessary, the aqueous phase was again acidified to pH 3 and extracted with ethyl acetate. The combined ethyl acetate extracts were shaken once with water, dried over Na₂SO₄, concentrated and dried again in a high vacuum. An amorphous substance was obtained. Yield 8.9 g (92%), m.p. 80°–90° C.

$[\alpha]_D^{23} = +4.2°$ (c=1, in methanol)

$C_{20}H_{30}N_2O_7$ (410.48)

calc. C 58.52; H 7.37; N 6.83; found C 58.8; H 7.5; N 6.5.

8. Ddz-Gly-Ile-Val-Glu(OBuᵗ)-Gln-ONb 4.48 ml (35 mmols) of N-ethylmorpholine and 8.47 g (41 mmols) of DCC were added at 0° C. to a solution of 15.8 g (38.5 mmols) Ddz-Gly-Ile-OH, 23.8 g (35 mmols) of H-Val-Glu(OBuᵗ)-Gln-ONb-trifluoroacetate and 5.2 g (38.5 mmols) of HOBT in 60 ml of dimethylformamide. The mixture was stirred for 1 hour at 0° C. for several hours at room temperature and left to stand overnight at room temperature. A jelly formed which was stirred into cooled NaHCO₃ solution. The reaction product was filtered off with suction and successively triturated with citrate buffer (pH 3), NaHCO₃ solution and water, each time filtered with suction and finally dried over P₂O₅. Yield 21.45 g (64%), m.p. 205°–207° C.

$[\alpha]_D^{25} = -12.3°$ (c=1, in methanol)

$C_{46}H_{67}N_7O_{15}$ (958.1)

calc. C 57.67; H 7.05; N 10.23; found C 57.6; H 7.2; N 10.0.

9. Ddz-Gly-Ile-Val-Glu(OBuᵗ)-Gln-OH 19.16 g (20 mmols) of Ddz-Gly-Ile-Val-Glu(OBuᵗ)-Gln-ONb were dissolved in a mixture of 100 ml of dimethylformamide and 100 ml of methanol. After addition of Pd/BaSO₄, the solution was catalytically hydrogenated. The hydrogenation was complete after 6 hours. The suspension was heated to about 70° C., the catalyst was filtered off from the hot solution and afterwashed with warm dimethylformamide. The filtrate was concentrated and the residue triturated with 100 ml of methanol. the mixture was left to stand overnight in the cooling chamber, filtered off with suction and afterwashed with cold methanol. The reaction product was dried in vacuo over P₂O₅. Yield 14 g (85%), m.p. 238°–241° C.

$[\alpha]_D^{29} = -13.3°$ (c=1, in methanol)

$C_{39}H_{62}N_6O_{13}$ (822.97)

calc. C 56.92; H 7.59; N 10.21; found C 56.0; H 7.6; N 10.8.

VI. Fragment condensation (1)

Ddz-Leu-Glu(OBuᵗ)-Asn-Tyr(Buᵗ)-Cys(Trt)-Asn-OBuᵗ

A solution of 6.6 g of DCC in 20 ml of dimethylformamide cooled to 0° C. was added to a solution, likewise cooled to 0° C., of 26.4 g (30 mmols) of Ddz-Leu-Glu(OBuᵗ)-Asn-Tyr(Buᵗ)-OH-hemihydrate, 16.0 g (30 mmols of H-Cys(Trt)-Asn-OBuᵗ and 4.05 g (30 mmols) of HOBT in 60 ml of dimethylformamide. The mixture was stirred for 2 hours at 0° C. and overnight at room temperature. The dicyclohexyl urea was filtered off with suction and washed with 20 ml of dimethylformamide. The filtrate was cautiously added, while stirring, to about 350 ml of cooled NaHCO₃ solution and extracted with 600 ml of ethyl acetate. The ethyl acetate phase was successively shaken once with 300 ml of NaHCO₃ solution, once with 300 ml of citrate buffer (pH 4) and once with 100 ml of NaHCO₃ solution, dried over Na₂SO₄ and concentrated. The residue was triturated with ether.

Yield 28–34 g (67–81%), m.p. 161°–165° C.

$[\alpha]_D^{25} = -13.1°$ (c=1, in CH₂—Cl₂)

$C_{74}H_{98}N_8O_{16}S$ (1387.73)

calc. C 64.05; H 7.12; N 8.07; S 2.31; found C 63.8; H 7.3; N 8.0; S 2.7.

2. H-Leu-Glu(OBuᵗ)-Asn-Tyr(Buᵗ)-Cys(Trt)-Asu-OBuᵗ-trifluoroacetate 27.75 g (20 mmols) of Ddz-Leu-Glu(OBuᵗ)-Asn-Tyr(Buᵗ)-Cys(Trt)-Asn-OBuᵗ were added at room temperature to a mixture of 17.5 ml of trifluoroacetic acid (0.2 mol), 3.5 ml of water and 330 ml of methylene chloride (about 350 ml of 5% trifluoroacetic acid with 1% water in methylene chloride). The mixture was stirred for 2 hours at room temperature, cooled to 0° C., the trifluoroacetic acid was neutralized with 17.75 ml (220 mmols) of pyridine and the mixture was concentrated in vacuo. The residue was dissolved in 250 ml of ethyl acetate and shaken three times, each time with 25 ml of water. The ethyl acetate phase was concentrated without previous drying. The residue was dried in a high vacuum and triturated with ether (instead of ether diisopropyl ether may be used). The residue was filtered off with suction, washed with ether and dried. Yield 25.2 g.

For further purification about 6 g portions were heated to boil in 30 ml of ethyl acetate and centrifuged while still hot. The precipitates were triturated twice with ether, centrifuged and dried in a high vacuum over P₂O₅. Yield 22.3 g (86%).

m.p. 178°–182° C., 161°–164°, 166°–171° C., $[\alpha]_D^{22} = +3.5°$ to 4.0° (c=1 in 90% strength acetic acid)

$C_{64}H_{85}N_8O_{14}SF_3$ (1279.5)

calc. C 60.08; H 6.70; N 8.76; S 2.51; found C 59.4; H 6.5; N 9.1; S 2.9.

amino acid analysis Asp (2.0); Glu (1.05); Cys (0.87); Leu (0.99); Tyr (1.05).

3. Ddz-Tyr(Buᵗ)-Gln-Leu-Glu(OBuᵗ)-Asn-Tyr(Buᵗ)-Cys(Trt)-Asn-OBuᵗ

9.7 g (16.5 mmols) of Ddz-Tyr(Buᵗ)-Gln-OH, 19.2 g (15 mmols) of H-Leu-Glu(OBuᵗ)-Asn-Tyr(Buᵗ)-Cys(Trt)-Asn-OBuᵗ.CF₃COOH and 2.025 g (15 mmols) HOBT were dissolved in 30 ml of dimethylformamide while stirring at room temperature. The mixture was then cooled to 0° C. and 1.95 ml (15 mmols) of N-ethylmorpholine and a solution of 3.3 g (16 mmols) of DCC in 9 ml of dimethylformamide were added. The mixture was stirred for 1 hour at 0° C. and for 4 hours at room temperature, and left to stand overnight at room temperature, the dicyclohexyl urea was filtered off with suction and washed twice with 4.5 ml each of dimethylformamide. The filtrate was added, while stirring, to 159 ml of saturated NaHCO$_3$ solution and the mixture was stirred until a pulverulent precipitate had formed. The precipitate was filtered off with suction, triturated with citrate buffer (pH 3), filtered off with suction, washed neutral with water and dried in a high vacuum. Yield 23.1 g. The crude substance was heated on the steam bath almost to boiling temperature, the thin suspension was placed overnight in the cooling chamber, the precipitate was filtered off with suction, washed with ethyl acetate and with ether. Yield 20 g (76.8%).

$[\alpha]_D^{24} = -10.2°$ (c=1, in methanol).

The substance decomposed from 205° C. on and carbonized at about 250° C.

C$_{92}$H$_{123}$N$_{11}$O$_{20}$S (1735.15)

| amino acid analysis | Asp | Glu | Cys | Leu | Tyr |
|---|---|---|---|---|---|
| calc. | 2.0 | 2.0 | 1.0 | 1.0 | 2.0 |
| found | 2.00 | 2.01 | 0.75 | 0.99 | 1.95 |

4.

H-Tyr(Bu$^t$)-Gln-Leu-Glu(OBu$^t$)-Asn-Tyr(Bu$^t$)-Cys(Trt)-Asn-OBu$^t$-trifluoroacetate 3.5 g (2 mmols) of Ddz-Tyr(Bu$^t$)-Gln-Leu-Glu(OBu$^t$)-Asn-Tyr(Bu$^t$)-Cys(Trt)-Asn-OBu$^t$ were dissolved in a mixture of 1.75 ml of trifluoro acetic acid (20 mmols), 0.35 ml of water and 33 ml of methylene chloride (about 35 ml of a 5% strength trifluoroacetic acid solution with 1% of water) and 3.5 ml of anisole while stirring. Stirring was continued for 3 hours at room temperature, 2 ml (24.8 mmols) of pyridine were added and the mixture was concentrated in a high vacuum. The residue was triturated with ether, filtered off with suction, washed with ether and dried. Next, the substance was triturated with water, filtered off with suction, washed with water and dried over P$_2$O$_5$. Yield 3.35 g.

For further purification the substance was heated for a short period of time almost to boiling temperature, with 20 ml each of ethyl acetate, filtered off while still hot, and washed with ether. Yield 3.0 g (92%), m.p. 255°–265° C. with decomposition.

$[\alpha]_D^{24} = -23.8°$ (c=1, in methanol)

C$_{80}$H$_{109}$N$_{11}$O$_{16}$S.CF$_3$COOH (1626.9)

| amino acid analysis: | Asp | Glu | Cys | Leu | Tyr |
|---|---|---|---|---|---|
| calc. | 2 | 2 | 1 | 1 | 2 |
| found | 1.95 | 2.08 | 0.81 | 1.07 | 2.04 |

5.

Ddz-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ 3.4 g (16.4 mmols) of DCC were added at 0° C. to a solution of 22.8 g (14 mmols) of H-Tyr(Bu$^t$)-Gln-Leu-Glu(OBu$^t$)-Asn-Tyr(Bu$^t$)-Cys(Trt)-Asn-OBu$^t$, 14.1 g (15.4 mmols) of Ddz-Ile-Cys(Trt)-Ser-Leu-OH.1 H$_2$O, 2.08 g (15.4 mmols) of HObt and 1.8 ml (14 mmols) N-ethylmorpholine in 70 ml of dimethylformamide.

The mixture was stirred for 1 hour at 0° C. and for 3 hours at room temperature, left to stand overnight at room temperature and the precipitate was filtered off with suction. The filtrate was concentrated in vacuo, the residue was successively triturated with NaHCO$_3$ solution, citrate buffer (pH 3), NaHCO$_3$ solution and water and each time filtered off with suction. Finally, the residue was dried over P$_2$O$_5$. Yield 33.18 g (99%).

For further purification the dry substance was suspended in 300 ml of warm ethyl acetate and heated on the steam bath for a short period of time. After the addition of 300 ml of ether, the warm mixture was filtered off with suction, washed with ether and dried, in a high vacuum. Yield 28.1 g (84%), m.p. 265°–270° C. with decomposition. $[\alpha]_D^{22} = -20.3°$ (c=1, in dimethylformamide).

Next, the reaction product was heated together with 100 ml of methanol, the mixture was left to stand in the cooling chamber (overnight), filtered off with suction and dried. Yield 23.75 g (71%), $[\alpha]_D^{22} = -25.4°$ (c=1 in dimethylformamide)

C$_{129}$H$_{169}$N$_{15}$O$_{25}$S$_2$ (2394.0)

| amino acid analysis: | Asp. | Ser | Glu | Cys | Ile | Leu | Tyr |
|---|---|---|---|---|---|---|---|
| calc. | 2 | 1 | 2 | 2 | 1 | 2 | 2 |
| found | 2.10 | 0.95 | 1.77 | 0.49 | 0.83 | 2.10 | 1.98 |

6.

H-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$-trifluoroacetate 24 g (about 10 mmols) of Ddz-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ were dissolved in a mixture of 8.75 ml (100 mmols) trifluoroacetic acid, 1.75 ml of water, 165 ml of methylene chloride (=about 175 ml of a 5% strength trifluoroacetic acid-methylene chloride solution with 1% of water) and 17.5 ml anisole while stirring. Stirring was continued for 4 hours at room temperature, 10 ml (124 mmols) pyridine were then added and the mixture was concentrated. The residue was triturated with ether, filtered of with suction, washed with ether and dried in vacuo. Next, the substance was triturated with water, filtered off with suction, washed with water and dried over P$_2$O$_5$.

For further purification the substance was boiled twice, each time with 100 ml of ethyl acetate and filtered off while still hot. Yield 22.7 g (99%), m.p. 234° C. with decomposition.

$[\alpha]_D^{26} = -11.7°$ (c=1, in dimethylformamide)

C$_{117}$H$_{155}$N$_{15}$O$_{21}$S$_2$.CF$_3$COOH (2285.8)

amino acid analysis:

| | Asp | Ser | Glu | Cys | Ile | Leu | Tyr |
|---|---|---|---|---|---|---|---|
| calc. | 2 | 1 | 2 | 2 | 1 | 2 | 2 |
| found | 2.05 | 0.99 | 1.88 | 0.43 | 0.73 | 2.12 | 2.05 |

7. Ddz-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ 1.7 g (8.25 mmols) of DCC were added at 0° C. to a solution of 16 g (7 mmols) of H-Ile-Cys(Trt)-Ser-Leu-Tyr(Bu$^t$)-Gln-Leu-Glu(OBu$^t$)-Asn-Tyr(Bu$^t$)-Cys(Trt)-

Asn-OBu$^t$-trifluoroacetate, 9.5 g (7.7 mmols) of Ddz-Cys(Trt)-Cys(Trt)-Thr(Bu$^t$)-Ser(Bu$^t$)-OH, 1.04 g (7.7 mmols) HOBt and 0.9 ml (7 mmols) of N-ethylmorpholine in 70 ml of dimethylformamide/dimethylacetamide mixture (1:1). The mixture was stirred for 2 hours at 0° C. and then at room temperature, left to stand overnight and again stirred on the following day for 5 hours at room temperature. The precipitated DC urea was filtered off with suction, the filtrate obtained was concentrated to half its volume in a high vacuum and added dropwise to ice water while stirring. The precipitate was filtered off with suction, successively washed witht NaHCO$_3$ solution, citrate buffer (pH 3), NaHCO$_3$ solution and water and dried over P$_2$O$_5$. For further purification the solid matter was stirred with 100 ml of ethyl acetate while heating, 200 ml of ether were added, the precipitate was filtered off with suction while still hot and dried. Next, the substance was heated in 220 ml of 50% strength aqueous methanol, then with 200 ml of methanol and each time filtered with suction while hot. Yield 19.42 g (81%), m.p. 250°–260° C. with decomposition.

$[\alpha]_D^{22} = -14.2°$ (c=1, in dimethylformamide)
C$_{188}$H$_{235}$N$_{19}$O$_{31}$S$_4$.2 H$_2$O (3421.4)
calc. C 66.00; H 7.04; N 7.78; S 3.75; found C 65.4; H 7.1; N 8.0; S 3.8.

amino acid analysis (after oxidation of cysteine to cysteinic acid):

|  | Asp | Thr | Ser | Glu | Cys | Ile | Leu | Tyr |
|---|---|---|---|---|---|---|---|---|
| calc. | 2 | 1 | 2 | 2 | 4 | 1 | 2 | 2 |
| found | 1.99 | 0.89 | 1.69 | 1.92 | 3.97 | 0.87 | 2.07 | — |

No tyrosine was found since it has been destructed during oxidation.

Amino acid analysis without oxidation:
found 2.08; 0.92; 1.87; 2.00; 1.55; 0.88; 2.00; 1.92.

8.
H-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu(OBu$^t$)-Asn-Tyr(BU$^t$)-Cys(Trt)-Asn-OBu$^t$-trifluoroacetate 10.26 g (3 mmols) of Ddz-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu-(OBu$^t$)-Asn-Tyr(Bu$^t$)-Cys(Trt)-Asn-OBu$^t$ were dissolved, while stirring, in a mixture of 5.25 ml (60 mmols) trifluoroacetic acid, 1.05 ml of water and 99 ml methylene chloride (about 105 ml of a 5% strength trifluoroacetic acid-methylene chloride solution with 1% of water) and 10.5 ml of anisole and stirring was continued for 4 hours at room temperature. Next, 10.5 ml pyridine were added and the mixture was concentrated, the residue was after-distilled in a high vacuum, the oily residue was triturated with ether, the precipitate was filtered of with suction and dried. Next, the substance was washed with water and dried over P$_2$O$_5$. For further purification it was boiled three times, each time with 100 ml of ethyl acetate and filtered off while still hot. Yield 7.96 g (81%), m.p. 240°–245° C. with decomposition.

$[\alpha]_D^{23} = -10.0°$ (c=1, in dimethylformamide).

C$_{176}$H$_{221}$N$_{19}$O$_{27}$S$_4$.CF$_3$COOH (3277.15)
amino acid analysis:

|  | Asp | Thr | Ser | Glu | Cys | Ile | Leu | Tyr |
|---|---|---|---|---|---|---|---|---|
| calc. | 2 | 1 | 2 | 2 | 4 | 1 | 2 | 2 |
| found | 1.96 | 0.80 | 1.49 | 2.03 | 3.21 | 1.10 | 2.04 | 1.78 |

9.
Ddz-Gly-Ile-Val-Glu(OBu$^t$)-Gln-Cys(Trt)-Cys(Trt)-Thr-(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ 0.13 ml of N-ethyl-morpholine and, at 0° C., 310 mg (1.5 mmols) of DCC were added to a solution of 3.28 g (1 mmol) of H-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$-trifluoroacetate, 1 g (about 1.2 mmols) of Ddz-Gly-Ile-Val-Glu (OBu$^t$)-Glu-OH and 162 mg HOBT (1.2 mmols) in 20 ml of dimethylformamide and dimethylacetamide (1:1). The mixture was stirred for 1 hour at 0° C. and for 6 hours at room temperature and left to stand overnight. A thick jelly was obtained to which ice water was added. The precipitate which formed was filtered off with suction, successively, triturated with NaHCO$_2$ solution, citrate buffer (pH 3), NaHCO$_3$ solution and water and each time filtered off with suction. The residue was washed with water and dried over P$_2$O$_5$. For further purification, it was boiled twice, each time with 25 ml of ethyl acetate and filtered off with suction while still hot. Yield 2.87 g (72%). m.p. 260°–278° C. with decomposition.

$[\alpha]_D^{24} = -24.5°$ (c=1, in dimethylformamide)
C$_{215}$H$_{281}$N$_{25}$O$_{39}$S$_4$ (3698.07)
amino acid analysis:

|  | Asp | Thr | Ser | Glu | Gly | Cys | Val | Ile | Leu | Tyr |
|---|---|---|---|---|---|---|---|---|---|---|
| calc. | 2 | 1 | 2 | 4 | 1 | 4 | 1 | 2 | 2 | 2 |
| found | 2.06 | 0.88 | 2.04 | 3.97 | 1.01 | 2.59 | 0.60 | 1.45 | 1.93 | 1.93 |

10.
H-Gly-Ile-Val-Glu(OBu$^t$)-Gln-Cys(Trt)-Cys(Trt)-Thr-(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$-trifluoroacetate 2.78 g (0.7 mmols) of Ddz-Gly-Ile-Val-Glu(OBu$^t$)-Gln-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$ were stirred for 4 hours at room temperature with 2.5 ml of anisole in 25 ml of a 5% strength trifluoroacetic acid-methylene chloride solution with 1% of water (about 14 mmols of trifluoroacetic acid). Then 1.4 ml of pyridine were added and the mixture was concentrated, first in a water jet vacuum and finally in a high vacuum. The residue was triturated with ether, filtered off with suction, washed with ether and dried. The substance was then triturated with water, filtered off with suction, washed with water and dried over P$_2$O$_5$. For further purification, the substance was boiled twice, each time with 30 ml of ethyl acetate and filtereed off while still hot. Yield 1.85 g (68.5%), m.p. 275°–280° C. with decomposition.

$[\alpha]_D^{23} = -24.0°$ (c=1, in dimethylformamide)
C$_{203}$H$_{267}$N$_{25}$O$_{35}$S$_4$.CF$_3$COOH (3859.8)
amino acid analysis:

|       | Asp  | Thr  | Ser  | Glu  | Gly  | Cys  | Val  | Ile  | Leu  | Tyr  |
|-------|------|------|------|------|------|------|------|------|------|------|
| calc. | 2    | 1    | 2    | 4    | 1    | 4    | 1    | 2    | 2    | 2    |
| found | 2.05 | 1.08 | 1.80 | 4.00 | 0.97 | 2.40 | 0.71 | 1.51 | 2.06 | 1.88 |

What is claimed is:

1. A process for the preparation of the peptide of the formula I as claimed which comprises:

H-Gly-Ile-Val-Glu(OBu$^t$)-Gln-Cys(Trt)-Cys(Trt)-Thr-(Bu$^t$)-Ser(Bu$^t$)-Ile-Cys(Trt)-Ser-Leu-Tyr(-Bu$^t$)Gln-Leu-Glu(OBu$^t$)-Asn-Tyr(Bu$^t$)-Cys(Trt)-Asn-OBu$^t$ (1) condensing
    a peptide of the formula II
        H-Cys(Trt)-Cys(Trt)-Thr(Bu$^t$)-Ser(Bu$^t$)-Ile-Cys(Trt)-Ser-Leu-Tyr(Bu$^t$)-Gln-Leu-Glu(OBu$^t$)-Asn-Tyr(Bu$^t$)-Cys(Trt)-Asn-OBu$^t$
    with a peptide of the formula III
        X-Gly-Ile-Val-Glu(OBu$^t$)-Gln-OH
by the dicyclohexylcarbodiimide method with the addition of N-hydroxy compounds, in said formula III, X is an amino protective group capable of being split off with 5% trifluoroacetic acid in methylene chloride and (2) selectively splitting off the amino protective group X from the obtained peptide with about 5% strength trifluoroacetic acid in methylene chloride.

2. The process as defined in claim 1 wherein the amino protective group X is 3,5-dimethoxy-α,α-dimethylbenzyloxycarbonyl group, diphenyl-isopropyloxycarbonyl group, and trityl group.

3. The process as defined in claim 1 wherein the amino protective group is split off with said trifluoroacetic acid-methylene chloride solution containing anisole and a small amount of water.

* * * * *